United States Patent [19]

Dormia

[11] Patent Number: 4,612,931

[45] Date of Patent: Sep. 23, 1986

[54] INSTRUMENT FOR EXTRACTING FOREIGN BODIES FROM PHYSIOLOGICAL CANALS OR DUCTS IN THE HUMAN BODY

[75] Inventor: Enrico Dormia, I-Lecco, Italy

[73] Assignee: Societe Anonyme: Synthelabo, Paris, France

[21] Appl. No.: 757,300

[22] Filed: Jul. 22, 1985

[30] Foreign Application Priority Data

Jul. 20, 1984 [IT] Italy ................. 21982 A/84

[51] Int. Cl.$^4$ ............................................ A61B 17/00
[52] U.S. Cl. ..................................... 128/328; 128/356
[58] Field of Search ................ 128/328, 356, 304, 756

[56] References Cited

U.S. PATENT DOCUMENTS

| | | | |
|---|---|---|---|
| 3,108,594 | 10/1963 | Glassman | 128/328 |
| 4,046,150 | 9/1977 | Schwartz et al. | 128/328 |
| 4,347,846 | 9/1982 | Dormia | 128/328 |

Primary Examiner—Richard J. Apley
Assistant Examiner—H. Macey
Attorney, Agent, or Firm—Fisher, Christen & Sabol

[57] ABSTRACT

This invention relates to an instrument for extracting foreign bodies from physiological canals or ducts in the human body, the instrument comprising a catheter containing an inner cable terminating in a slide on which is mounted an outer basket which moves the walls of the physiological canal apart and this outer basket contains therewithin a basket for extracting the foreign body; the spacer basket thus maintains the walls of the physiological canal away from any rough edges of the body to be extracted, thus preventing the edges from injuring the walls. The invention is more particularly applicable to a catheter for extracting calculi from physiological canals or ducts.

7 Claims, 3 Drawing Figures

INSTRUMENT FOR EXTRACTING FOREIGN BODIES FROM PHYSIOLOGICAL CANALS OR DUCTS IN THE HUMAN BODY

The present invention relates to an instrument for extracting foreign bodies from the physiological ducts or canals in the human body.

Such foreign bodies may consist for example in calcareous concretions (calculi) or the like. An instrument of the type specified hereinabove is already known, which is essentially constituted by an outer tube or catheter made of flexible material inside which is mounted a fine cable supporting the operational part of the instrument, said operational part being constituted by a plurality of elastic filamentary elements, advantageously made of stainless steel. These filamentary elements are fixed at their proximal ends to the distal end of said cable. These elements are assembled together at their distal ends, advantageously with the aid of an endpiece or ogive of rounded section. Before they are joined by a common distal endpiece as mentioned hereinabove, these elastic filamentary elements, in the operational position of the catheter, are twisted, for example in helicoidal manner, starting from the weld of the distal end of said metal wires; in this way, the latter follow a widened shape constituting a basket or cage in the open position of the catheter. The number of filamentary elements, and their exact shape or section, may vary as desired, as long as these filamentary elements form a basket.

During use, the part which constitutes the basket is firstly closed and returned inside the the distal end of the catheter and the latter is engaged in the physiological canal or duct until this distal end lies beyond the zone where the calculi or other foreign bodies are located. At that level, the basket is returned into expanded position and the elastic wires abut against the walls of the canal or duct as a function of the width thereof and the basket is then returned rearwardly towards the foreign body, so as to imprison it and allow it to be extracted.

In practice, it has been observed that operation of this type of apparatus is not without drawbacks. In fact, by reason of the irregular shape of the foreign bodies which may for example be rough or have sharp protuberances, it is observed that these foreign bodies, in the movement of extraction, come into position in the distal zone of the basket, and their sharp points project beyond this zone through the wires of the basket and come into contact with the wall of the canal or duct in question; under these conditions, the sharp points of the foreign bodies, when the latter are displaced, may injure and cut through the inner wall of the canal, this necessitating a surgical operation.

It is an object of the present invention to create an instrument of the type specified hereinabove which allows foreign bodies to be extracted without agression of the wall of the canal and which prevents the rough parts of the foreign bodies from coming into contact with the inner wall of the canal whilst the instrument is being manoeuvred.

The invention therefore relates to an instrument for extracting foreign bodies from physiological canals or ducts in the human body and of the type comprising a tube or catheter receiving a control cable connected at its distal end to a spacer basket or cage formed by elastic wires, this instrument being characterized in that:

(a) inside the spacer basket there is provided an extracting basket shaped in similar manner;

(b) the inner extracting basket is connected by its proximal end to the proximal end of the spacer basket and the distal end of the extracting basket is independent and spaced apart from the distal end of the outer spacer basket; and (c) between the inner extracting basket and the outer spacer basket is thus defined an intermediate volume adapted to contain the rough edges or protuberances of the foreign bodies to be extracted.

Thus, when the instrument according to the invention is used in an operation of extraction, the inner wall of the physiological canal or duct cannot be cut or injured in any way by the rough edges or protuberances of a foreign body being carried along; in fact, this foreign body is imprisoned in the inner basket and under these conditions any rough edges or protuberances of the foreign body are housed within the intermediate volume defined between the virtual surface of envelopment of the inner basket and that of the outer basket, without damaging the inner wall of the physiological canal.

In practice, lesions are avoided with certainty by providing a length of the inner basket corresponding approximately to half the length of the outer basket. As far as the directions of spiral twist of the outer basket and that of the inner basket are concerned, the twists may be in register or they may be provided with a winding in opposite direction. Similarly, the numbers of wires of the spacer basket and of the extracting basket may be equal or different. The sections of the wires of the two baskets may be different.

The shape of the apparatus according to the invention does not increase the dimensions and the apparatus according to the invention may present the same dimensions as the instruments known at the present time.

The apparatus according to the invention also presents advantages from the constructional standpoint; in fact, it is constructed in accordance with the same standards which were defined for the conventional instruments.

The intermediate zone provided between the virtual surface of envelopment of the baskets advantageously presents a maximum volume at the level of the distal part of the inner basket.

The invention will be more readily understood on reading the following description with reference to the accompanying drawings, in which.

Figure 1:
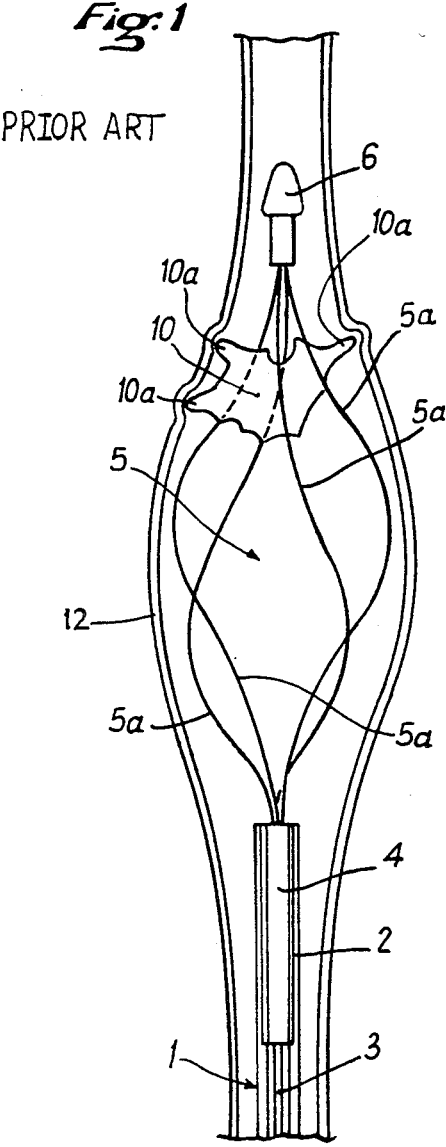
FIG. 1 shows a view in longitudinal section through a physiological canal or duct in which is engaged an apparatus for extracting foreign bodies, of known type.

Referring now to the drawings, in which like parts or members bear the same references, the instrument for extracting foreign bodies is generally referenced 1. In FIG. 1, the apparatus is constituted by a catheter 2 or the like internally containing a fine cable 3 of which the upper end terminates in a slide 4. At the top of the latter is fixed, for example by welding, the lower end of the spacer and extracting basket 5. The latter, which is an extractor of known type, performs the double function of constituting a spacer basket and an extracting basket and it is formed by a plurality of metal wires 5a. These latter follow a twisted path, for example of helicoidal type, are fixed and joined together at their upper ends, advantageously by means of a weld, to an ogival endpiece 6. When the wires 5a have emerged from the catheter 2, they resume the shape of a basket, shown in the drawings, due to their elastic nature.

Figure 2:
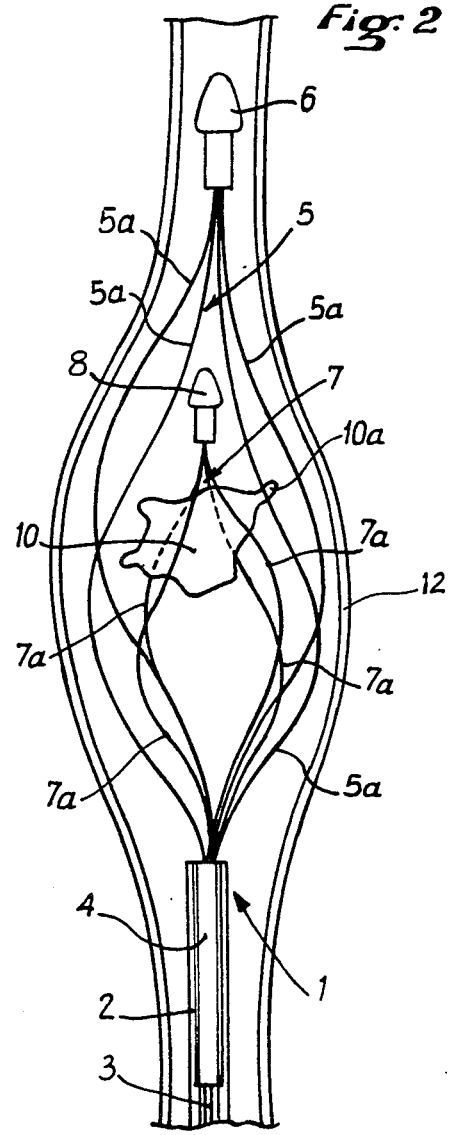
FIG. 2 shows a view in longitudinal section similar to FIG. 1 and presenting an apparatus for extracting foreign bodies according to the invention.
Figure 3:
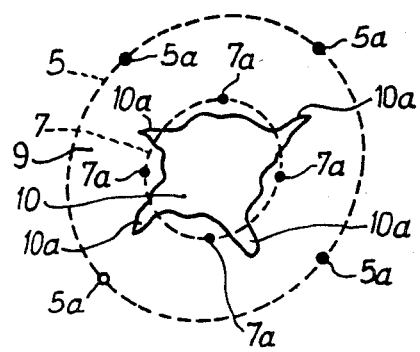
FIG. 3 shows a transverse section through FIG. 2 at the level of the foreign body to be extracted.

The instrument according to the invention which is shown in FIG. 2 is shaped similarly to that of FIG. 1, but with the difference that the basket 5 performs only the function of spacer basket. Within this basket there is positioned an inner basket 7, which is formed by a plurality of wires 7a spirally wound in the same way as the wires 5a of basket 5. The basket 7 presents a height which is substantially less than that of the outer basket 5 and the upper end of basket 7 terminates in an ogival endpiece 8. Independently of the direction of wind of wires 5a and 7a, the virtual surfaces of envelopment of baskets 7 and 5 define therebetween an intermediate zone or volume 9 (FIG. 3) provided to receive or imprison any rough edges or protuberances 10a of the foreign body 10 to be extracted; in this way, such rough edges 10a or the like cannot come into contact with the inner wall 11 of the physiological canal 12, as was the case in instruments of known type as shown in FIG. 1. Any possibility of cutting or injuring the inner wall of the physiological canal is thus eliminated and surgical operations possibly resulting from lesions consecutive to the use of the prior known apparatus are thus avoided.

It is clear from the foregoing that the instrument according to the invention effectively solves the problem raised and enables the advantages described hereinabove to be obtained. In particular, internal lesions or agressions are avoided whilst conserving simplicity of construction and convenience of handling of the prior known apparatus. In practice, the shape to be given to the wires of the baskets, their direction of rotation or their curvilinear section, and their number, may be adapted or modified as desired without departing from the field of protection of the present invention. Likewise, the height of the inner basket may be chosen freely.

In practice, it has been observed that the best results are obtained by adopting for the inner basket 7 a height which is subsantially half the height of the outer basket 5. The dimensions and materials (possibly in the form of laminated materials or comprising a coating) may also be modified as desired. The instrument is applicable both in the domain of medicine and in the veterinary field.

What is claimed is:

1. In an instrument for extracting foreign bodies from physiological canals or ducts in the human body, comprising a tube or catheter containing a control cable in turn supporting a basket or cage formed by elastic wires,
   (a) said basket constitutes an outer spacer basket and it contains therewithin an inner extracting basket shaped in similar manner;
   (b) the inner extracting basket is connected by its proximal end to the proximal end of the spacer basket and the distal end of the inner extracting basket is independent and spaced apart from the distal end of the outer spacer basket; and
   (c) between the inner extracting basket and the outer spacer basket is defined an intermediate volume adapted to contain the rough edges or protuberances of the foreign bodies to be extracted.

2. The instrument for extracting foreign bodies of claim 1, wherein the outer spacer basket and the inner extracting basket present the same number of wires.

3. The instrument of claim 1, wherein the outer spacer basket and the inner extracting basket present a different number of wires.

4. The instrument of claim 1, wherein the wires of the outer basket and of the inner basket are provided with a winding in the same direction.

5. The instrument of claim 1, wherein the wires of the outer basket and of the inner basket are provided with windings of opposite directions.

6. The instrument of claim 1, wherein the length of the inner basket is substantially equal to half the length of the outer basket.

7. The instrument of claim 1, wherein the baskets are constituted by wires presenting different transverse sections.

* * * * *